Sept. 28, 1965 E. S. BOERNER Plant Pat. 2,552
CHRYSANTHEMUM PLANT
Filed May 7, 1964
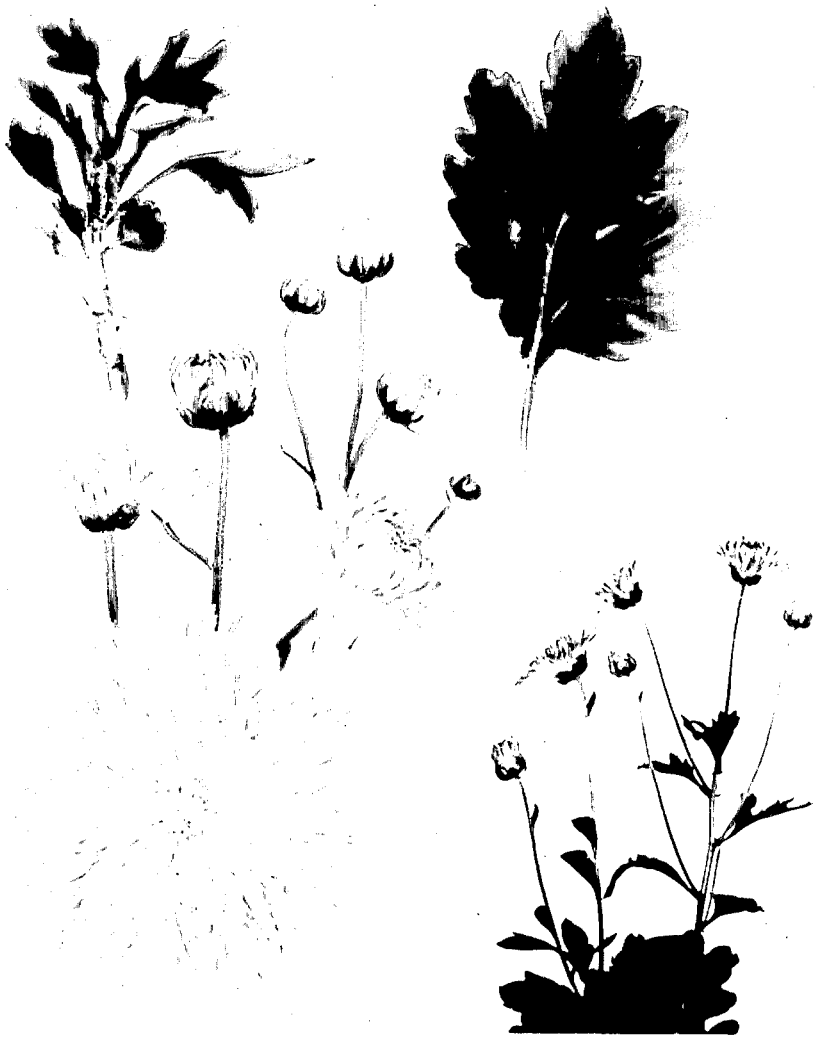
Inventor.
E. S. Boerner
By: Robb & Robb
Attorneys.

United States Patent Office

Plant Pat. 2,552
Patented Sept. 28, 1965

2,552
CHRYSANTHEMUM PLANT

Eugene S. Boerner, Newark, N.Y., assignor to Jackson & Perkins Company, Newark, N.Y., a corporation of New York Filed May 7, 1964, Ser. No. 365,849
1 Claim. (Cl. Plt.—81)

The present invention relates to a new and distinct variety of chrysanthemum plant of the decorative class, which was originated by me by crossing the variety known as "Tanager" (Plant Patent No. 1,129) with an unnamed and unpatented seedling of the chrysanthemum variety known as "Kingfisher" (Plant Patent No. 1,548).

The primary objective of this breeding was to produce a new chrysanthemum variety having the hardiness and vigor of the parent variety "Tanager," combined with the flower color and good thickness of the variety "Kingfisher." This objective was fully achieved, as evidenced by the following unique combination of characteristics which are outstanding in the new variety and which distinguish it from its parents, as well as from all other varieties of which I am aware:

(1) Strong, vigorous, and winter hardy plant habit;
(2) A thick flower form; and
(3) A distinctive and attractive general color tonality of the flowers corresponding to Spinel Pink, lightly overcast with Rose Color.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen plant which is depicted in black-and-white for the purpose of illustrating the form and habit of growth of the plant.

The following is a detailed description of the new variety, with color terminology in accordance with Ridgway's Color Standards and Nomenclature, as based upon observations of specimens grown outdoors at Newark, New York, in the afternoon during the first part of the month of October:

Parentage: Seedling.
*Seed parent.*—"Tanager."
*Pollen parent.*—Unnamed seedling of "Kingfisher."
Classification: Decorative.
Growth: Free and branching.

Cold resistance: Very winter hardy in northern New York State.
Blooming period: In Newark, New York climatic area—date of start of bloom—mid-September continuing until freezing weather.

*Flower*

Bud:
*Color.*—When petals first divide—Hellebore Red, Plate 38. When petals begin to unfurl—Spinel Red, Plate 26, lightly overcast with Spinel Pink, Plate 26. When half-blown:—inside—Tyrian Rose, Plate 12, lightly overcast with Spinel Pink, Plate 26; outside—Tyrian Rose, Plate 12, lightly overcast with Spinel Pink, Plate 26.
*Peduncle.*—Color—Light Cress Green, Plate 31. Strength—medium.

Bloom:
*Size.*—5 inches in diameter.
*Stem.*—Medium thickness.
*Form.*—Thick decorative; 3 inches thick.
*Petalage.*—Very double.
*Color.*—Center of flower—Spinel Red, Plate 26, lightly overcast with Spinel Pink, Plate 26. Outer petals—Rose Color, Plate 12. Base of petals—Chartreuse Yellow, Plate 31. Inside of petals—Spinel Pink, Plate 26, lightly overcast with Rose Color, Plate 12. Reverse of petals—Rose Color, Plate 12, overcast lightly with Deep Rose Pink, Plate 12.
*Petals.*—Texture—medium thickness. Form—oval.
*Fragrance.*— Characteristic chrysanthemum.

*Plant*

Form: Branching.
Growth: Very free.
Foliage:
*Size.*—Large.
*Quantity.*—Normal.
*Color.*—Upper side—Empire Green, Plate 32. Reverse side—Cress Green, Plate 31.
*Texture.*—Leathery.

I claim:

A new and distinct variety of chrysanthemum plant of the decorative class, substantially as herein shown and described, characterized particularly as to novelty by the unique combination of a strong, vigorous, and winter hardy plant habit, a thick flower form, and a distinctive and attractive general color tonality of the flowers corresponding to Spinel Pink, lightly overcast with Rose Color.

No references cited.

ABRAHAM G. STONE, *Primary Examiner.*